United States Patent [19]
Namenye et al.

[11] Patent Number: 5,443,488
[45] Date of Patent: Aug. 22, 1995

[54] THERMAL BLANKET WITH SURGICAL ACCESS

[75] Inventors: Joseph A. Namenye, Elkhart, Ind.; James G. Stephenson, Marshall, Mich.; Corrie T. M. Anderson, Woodland Hills, Calif.

[73] Assignee: Progressive Dynamics, Inc., Marshall, Mich.

[21] Appl. No.: 290,523

[22] Filed: Aug. 15, 1994

[51] Int. Cl.[6] .............................................. A61F 7/00
[52] U.S. Cl. ................................. 607/104; 607/107; 607/114; 165/46
[58] Field of Search .................... 607/104–107, 607/108–112, 114; 165/46; 126/204; 5/421–423, 482, 485; 4/535–537; 62/252.3

[56] References Cited

U.S. PATENT DOCUMENTS

| | | | |
|---|---|---|---|
| 1,777,982 | 10/1930 | Popp | 607/104 |
| 2,601,189 | 6/1952 | Wales, Jr. | 5/482 |
| 3,830,676 | 8/1974 | Elkins | 165/46 |
| 4,572,188 | 2/1986 | Augustine | 607/107 |
| 4,660,388 | 4/1987 | Greene, Jr. | 607/104 |
| 4,777,802 | 10/1988 | Feher | 62/261 |
| 4,867,230 | 9/1989 | Voss | 165/46 |
| 5,125,238 | 6/1992 | Ragan et al. | 62/529.3 |
| 5,165,400 | 11/1992 | Berke | 607/104 |
| 5,241,951 | 9/1993 | Mason et al. | 607/104 |
| 5,265,599 | 11/1993 | Stephenson et al. | 607/104 |
| 5,304,213 | 4/1994 | Berke et al. | 607/104 |

Primary Examiner—Lee S. Cohen
Assistant Examiner—Robert L. Nasser, Jr.
Attorney, Agent, or Firm—Beaman & Beaman

[57] ABSTRACT

A disposable pneumatic thermal blanket for controlling a patient's body temperature wherein the blanket includes structure for providing access through the blanket for surgical purposes. The inflatable blanket consists of upper and lower thermoplastic sheets heat sealed at the periphery and specified locations and sealed slits within the blanket central region permit access to a patient without loss of temperature controlled air. The blanket includes strategically placed adhesive strips or patches to aid the positioning of folded blanket access portions, or positioning of the blanket on the patient, and the location and relationship of the slits permit a variety of shapes and sizes of access openings to be selectively formed.

20 Claims, 4 Drawing Sheets

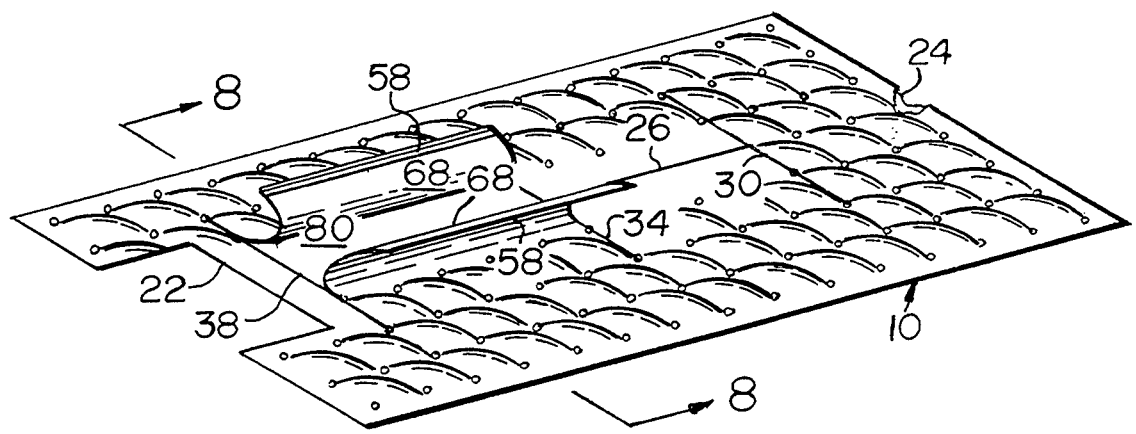
_Fig_-7
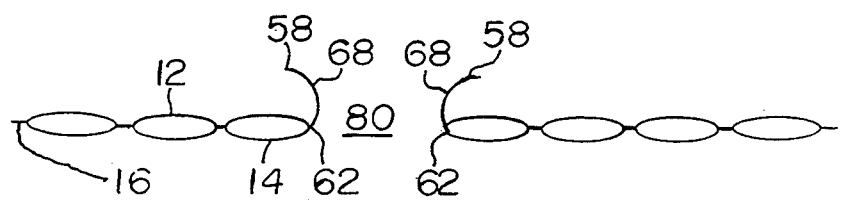
_Fig_-8
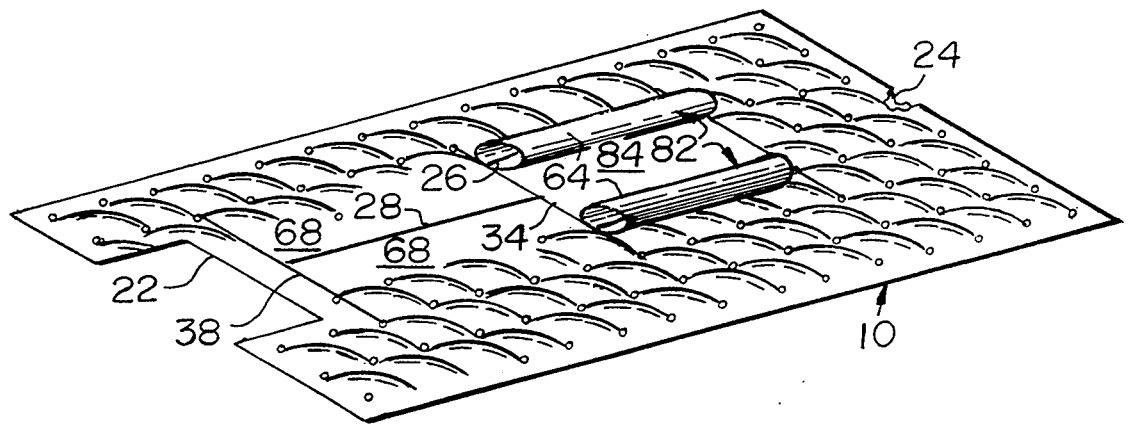
_Fig_-9

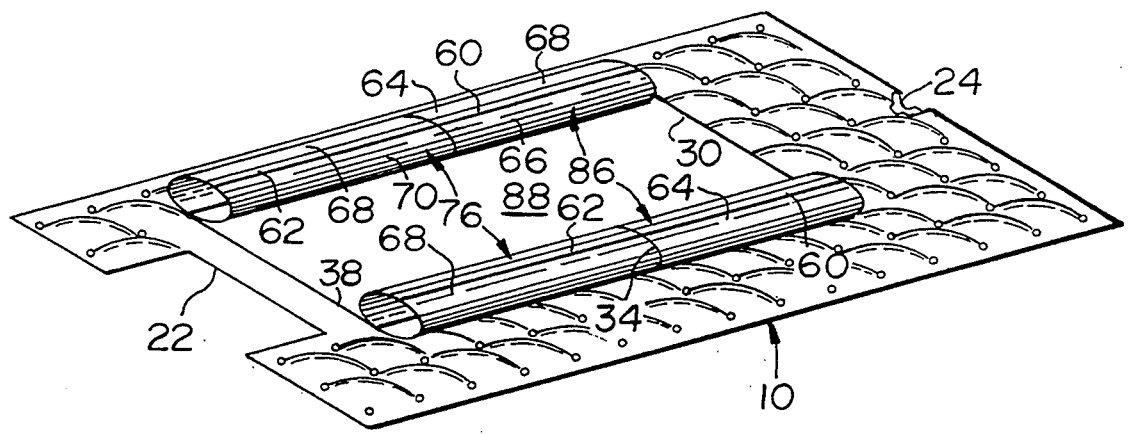

THERMAL BLANKET WITH SURGICAL ACCESS

BACKGROUND OF THE INVENTION

1. Field of the Invention

The invention pertains to temperature controlled pneumatic disposable blankets to aid the control of a patient's body temperature and yet provide access through the inflated blanket for surgical purposes or the like.

2. Description of the Related Art

During surgery, and thereafter, and in a number of other medical circumstances, it is desirable to bathe the patient's body with a controlled temperature air, usually heated, to reduce the likelihood of trauma and thermal shock, and for the purpose of controlling body temperature in order to achieve the most advantageous medical conditions in a specific instance.

A common type of thermal blanket consists of an envelope defined by upper and lower flexible sheets which is inflated by a temperature controlled air under slightly superatmospheric pressure, and the air impinges on the patient's body through a plurality of orifices formed in the lower sheet. Typical thermal blankets are shown in U.S. Pat. Nos. 1,777,982; 2,601,189; 4,572,188; 4,660,388; 4,777,802; 4,867,230 and 5,165,400.

Blankets of this type are also shown in U.S. Pat. Nos. 5,125,238 and 5,256,599 in which an inventor of this application is an inventor, and such patents are assigned to the assignee of this application.

While such thermal blankets as identified above are capable of distributing temperature controlled air over a patient's body, the blanket covers the patient's entire body and it is not possible to simultaneously access the patient, for surgical purposes, for instance, while the blanket lays upon the patient and is providing temperature regulation.

Difficulty is encountered in endeavoring to provide a surgical access through a pneumatic thermal blanket utilizing superatmospheric temperature controlled air in that the openings formed in the blanket necessary to provide access will permit the temperature regulated air to escape, and such access will interfere with the thermal regulation desired to be achieved by the blanket.

OBJECTS OF THE INVENTION

It is an object of the invention to provide an inflatable disposable patient temperature control blanket having structure to provide a surgical access through the blanket without negatively affecting the blanket inflation.

Another object of the invention is to provide an inflatable disposable temperature control blanket having surgical access means defined therein wherein the size and configuration of the access opening may be selectively determined to accommodate use for the type of access required, and wherein the blanket is capable of maintaining the desired access opening configuration.

Yet another object of the invention is to provide an inflatable disposable temperature control blanket having selectively usable surgical access openings defined therein wherein the openings are sealed with respect to the superatmospheric air within the blanket, and wherein the inflation of the blanket does not interfere with the shaping and sizing of the desired blanket access opening.

A further object of the invention is to provide a disposable thermal control blanket utilizing superatmospheric temperature controlled air wherein the blanket includes adhesive patches which may be selectively employed to adhere the blanket to the patient's body for maintaining positioning thereon, and maintain the shape of surgical access openings defined in the blanket.

SUMMARY OF THE INVENTION

The basic configuration and construction of a disposable pneumatic thermal control blanket for medical purposes is shown in the assignee's U.S. Pat. No. 5,125,238. This patent discloses a disposable temperature control inflatable blanket consisting of upper and lower thermoplastic flexible sheets heat sealed together at the sheet peripheries, and intermittently staked at spaced locations within the periphery to control inflation. The upper sheet, which is the sheet disposed away from the patient, is air impervious, while the lower sheet includes a plurality of orifices through which the temperature controlled air within the blanket envelope escapes and is directed downwardly upon the patient's body for controlling the temperature of the patient. Preferably, the blanket lower sheet is formed of a material having a greater coefficient of friction than the upper blanket to aid in maintaining the blanket upon the patient's body, and the temperature controlled air is supplied to the blanket through a fitting usually located at the foot end edge of the blanket.

Because the blanket is economically manufactured and formed of thin flexible sheet material, and as the air supply fitting is preferably formed of a folded heavy duty paper material, the blanket may be concisely folded and stored prior to use, and its low cost permits the entire blanket to be disposed of after a single use, eliminating the need for expensive laundering, and as each blanket may be sterile packaged, its cleanliness prior to usage is guaranteed. In the practice of the invention, a pneumatic disposable temperature control blanket such as shown in U.S. Pat. No. 5,125,238 is provided with structure capable of defining an access opening within the central region of the blanket through which surgical procedures, or the like, may be accomplished. As the blanket will remain upon the patient during surgery, those portions of the blanket which have not been displaced to provide the access may continue to impinge temperature controlled air upon the patient for body temperature control purposes.

The access opening through the blanket is provided by a plurality of perforated slits extending through the blanket upper and lower sheets. The perforations initially hold the shape of the blanket during shipping and handling and weaken the blanket so that the desired slits may be formed by fracturing the perforations merely by pulling the blanket envelope portions apart upon opposite sides of the slits, and in this manner the desired opening configuration may be produced.

The upper and lower blanket sheets are heat sealed together on opposite sides of the slits' to prevent the pressurized air within the blanket envelope from escaping. Preferably, the slits include an elongated primary linear central slit located within the blanket central region intermediate the blanket lateral sides, and substantially parallel thereto. The central slit may extend approximately three-quarters the length of the blanket. The central slit is intersected by several secondary transverse slits disposed at right angles to the central slit and extending therethrough. The secondary slits are spaced from each other along the length of the central primary slit, and the portions of the blanket between the secondary slits, in conjunction with the central slit, define flap portions whereby the flap portions may be folded back over the upper blanket sheet thereby providing access through the blanket. Normally, both opposed flap portions will be folded away from each other to define the desired access opening.

In the preferred embodiment, a secondary central transverse slit intersects the primary central slit, and two secondary end transverse slits intersect the ends of the central slit wherein four major flap portions will be defined in the blanket. The opposite sides of each slit will be heat sealed to prevent the loss of the air within the blanket envelope and the use of three secondary transverse slits selectively permits an access opening to be located at the patient's chest region, or abdomen region, or if desired, all four major flap portions may be folded back exposing the patient's entire torso.

Adhesive patches are located on the blanket lower sheet having shields disposed over their adhesive face whereby selective adhesive patches may be used for adhesive purposes, as desired. For instance, adhesive patches are preferably located adjacent the secondary slits at the central slit ends and on the opposite side thereof with respect to the central slit, whereby such adhesive patches permit adhering to the patient's skin for maintaining the blanket position on the patient.

Also, adhesive patches are placed on the blanket lower sheet on either side of the central slit at the central slit opposite edges whereby, upon folding of the flap portions away from each other such adhesive patches may be used to hold the flap portions in an open condition by adhering the edges of the flap portion adjacent the central slit to the blanket upper sheet. Additionally, adhesive patches are placed upon the lower sheet spaced from the central slit, and parallel thereto, so that such patches may be used to adhere the blanket to the patient when the flap portions are folded back to provide access through the blanket.

Another feature of the invention includes the possible use of a heat seal between the upper and lower sheets parallel to the primary central slit, and spaced therefrom, whereby the outer portion of the flap portions adjacent the central slit will not be inflated to facilitate the folding back of the flap portions to provide the access opening.

The concepts of the invention are all incorporated into a disposable, temperature control blanket capable of being concisely folded and stored, and high production manufacturing techniques permit the slits, heat seals and adhesive patches to be economically incorporated into the blanket.

BRIEF DESCRIPTION OF THE DRAWINGS

The aforementioned objects and advantages of a disposable, temperature control blanket in accord with the inventive concepts will be appreciated from the following description and accompanying drawings wherein:

FIG. 7 is a perspective view of the inflated blanket illustrating a small access opening being formed in the patient's chest region, the flap portions being folded back, but not adhered to the blanket upper sheet, FIG. 8 is an elevational sectional view taken along Section 8—8 of FIG. 7, FIG. 9 is a perspective view of an inflated blanket in accord with the invention illustrating an access opening being formed in the lower region of the blanket of a smaller dimension, the flap portions adhering to the upper sheet, FIG. 10 is a perspective view of the blanket illustrating the maximum dimension access opening capable of being formed wherein the patient's entire torso is accessible, FIG. 11 is a perspective view of the blanket illustrating partial folding of the flap portions to provide a diamond shaped access opening at the blanket central region, and FIG. 12 is a perspective view of another embodiment of a blanket in accord with the inventive concepts wherein the central primary slit extends to the foot edge of the blanket, and the air supply port is located at the blanket head end.

DESCRIPTION OF THE PREFERRED EMBODIMENTS

Figure 1:
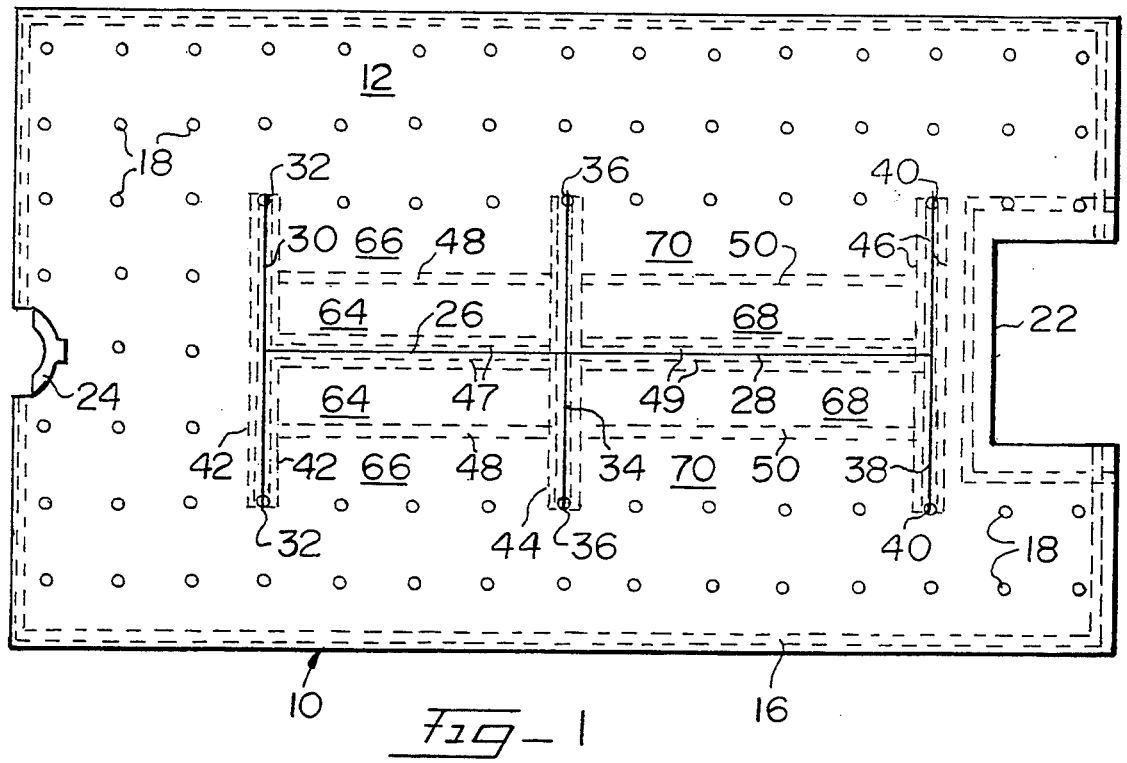
FIG. 1 is a top plan view of the upper sheet of a blanket in accord with the invention prior to the opening of an access opening.

A disposable pneumatic temperature control blanket in accord with the inventive concepts is generally indicated at 10 in the drawings. The blanket 10 consists of an envelope defined by an upper layer 12 of a thermoplastic air impervious flexible sheet 12 sealed to a lower thermoplastic flexible sheet 14. Preferably, the outer surface of the sheet 14 is provided with a friction material as may be formed of a fibrous composition, and the sheets 12 and 14 are heat sealed at their periphery by the heat seal seam 16 to form an envelope. Within the periphery heat seal 16, the sheets 12 and 14 are tacked together by heat seal welds 18 located at spaced locations to control the degree of inflation of the blanket envelope.

A plurality of orifices 20 are defined in the lower sheet 14 and are preferably formed of a Y configuration to define valve flaps as described in U.S. Pat. No. 5,246,656. The blanket includes a neck opening 22, and the temperature regulated superatmospheric pressurized air is introduced into the blanket envelope by a hose, not shown, through the inlet fitting port 24 located at the foot end of the blanket envelope.

The aforedescribed disposable thermal blanket construction is identical to that disclosed in the assignee's U.S. Pat. No. 5,125,238 and the operation and use of the blanket will be appreciated from such disclosure, and is incorporated herein by reference.

The blanket 10 is provided with a plurality of slits which, as later described, form the surgical access openings in the blanket to permit the blanket 10 to be used during surgery procedures, and yet provide access to the patient's body. The blanket 10 includes the linear slit 26 defined by a plurality of perforations which are located between the lateral edges of the sheets 12 and 14, and extends through the sheets. A second set of slit perforations 28 constitutes an extension of the perforations 26 and in line therewith and extending toward the neck opening 22. The slit perforations 26 and 28 constitute a primary slit extending substantially three-quarters of the distance between the neck opening 22 and the foot end of the blanket, and at its foot end the slit perforations 26 are intersected by the secondary slit perforations 30 which are perpendicularly related to the slit perforations 26, and extend across the perforations 26. The slit perforations 30 terminate at their ends 32.

Another secondary set of slit perforations 34 are parallel to the perforations 30 and are spaced therefrom along the length of the primary slit perforations 26–28. The secondary slit perforations 34 perpendicularly intersect the perforations 26–28 and terminate at the ends 36.

At the head end of the blanket, a third set of secondary transverse slit perforations 38 perpendicularly intersect the slit perforations 28 and are defined by the ends 40, FIG. 1.

To prevent the escape of the superatmospheric air within the blanket envelope through the slit perforations 30, the upper sheet 12 and the lower sheet 14 are heat sealed in an elongated linear manner on opposite sides of the slit perforations 30 as indicated at 42, FIG. 1. In a like manner, the slit perforations 34 are heat sealed on each side by heat seals 44, and the slit perforations 38 are heat sealed on each side by the heat seals 46, FIG. 1.

In order to prevent the escape of air at the slit perforations 26, the opposite edges of the perforations 26 are heat sealed by elongated seals 47, FIG. 1, and heat seals 48 parallel to the heat seals 47 extend between the heat seals 42 and 44 preventing the air within the blanket envelope from entering that portion of the blanket envelope flap portions adjacent the slit perforations 26, as later described.

In a similar manner, the heat seals 49 located adjacent slit perforations 28 will maintain the sheets bonded together, and heat seals 50, FIG. 1, parallel to seals 49 will prevent the superatmospheric air within the blanket from entering the blanket flap portions defined by the slit perforations 28, as later described.

Figure 2:
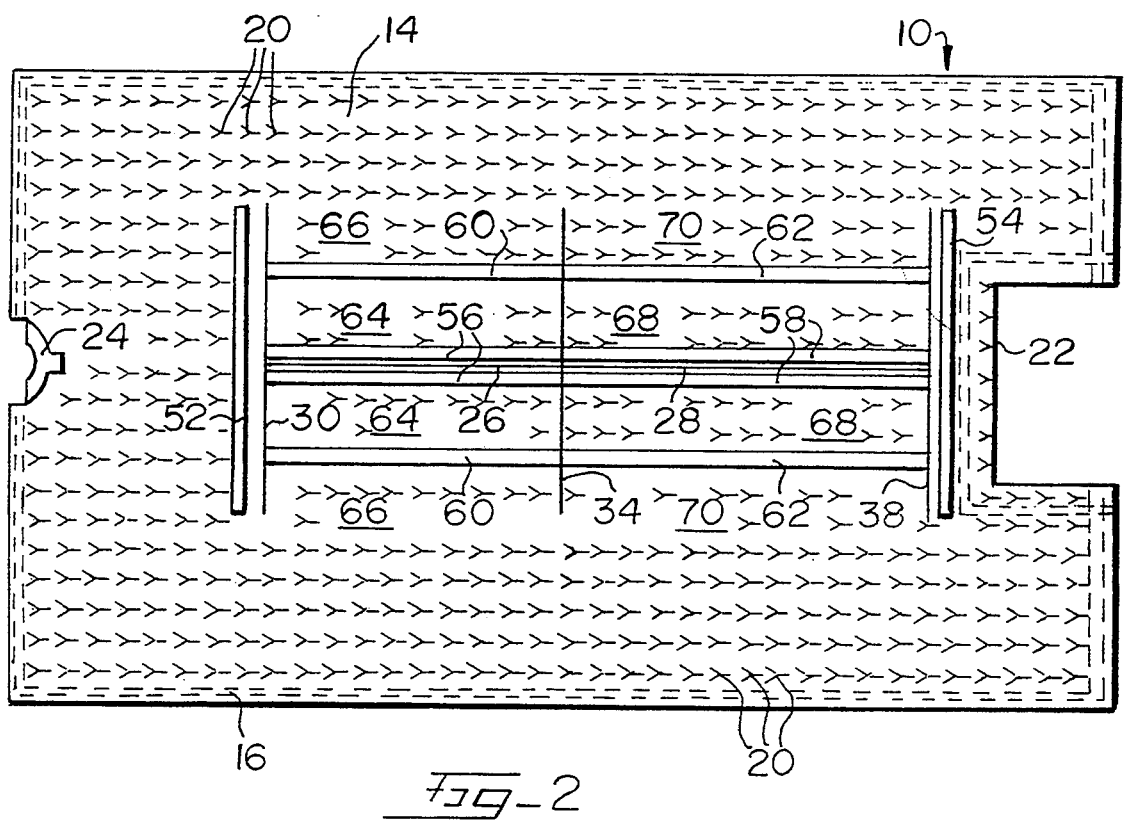
FIG. 2 is a bottom view of the lower sheet of the blanket as shown in FIG. 1.

With reference to FIG. 2, the underside of the blanket 10 is illustrated. It is to be noted that in FIG. 2 the heat seal stakes 18 are not illustrated for purpose of simplifying the drawing, but the stakes 18 are normally visible from the blanket underside.

An elongated adhesive tape or patch 52 is located adjacent the slit perforations 30 parallel thereto and located on the side opposite the slit perforations 30 with respect to the slit perforations 26. In the illustrated embodiment, the length of the adhesive patch 52 is substantially equal to the length of the slit perforations 30, while other configurations are anticipated, and the adhesive patch preferably consists of a conventional double sided adhesive faced tape wherein one side adheres to the blanket lower sheet 14, while the exposed outer adhesive face will normally be covered by a shield of release paper or the like, which is peeled off and removed from the adhesive material when it is desired to use the adhesive characteristics of the patch 52. Such double sided adhesive tape is well known, as is the use of the removable shield to selectively expose the adhesive material.

A similar adhesive patch 54 is located at the head end of the blanket 10 adjacent the slit perforations 38 as will be appreciated from FIG. 2. Additionally, elongated adhesive tapes or patches 56 are located on the opposite edges of the slit perforations 26 extending between the slit perforations 30 and 34, and in a similar manner, adhesive tape patches 58 are located upon opposite sides of the slit perforations 28 extending between the slit perforations 34 and 38.

As also visible in FIG. 2, adhesive tapes 60 are mounted upon the lower sheet 14 parallel to the tapes 56 and in opposed relation to heat seals 48, and spaced from the slit perforations 26 about five inches. In a similar manner, the adhesive tapes 62 are located parallel to and spaced from the slit perforations 28 between the slit perforations 34 and 38 in opposed relation to the heat seals 50, and are in alignment with the tape perforations 60, as will be appreciated in FIG. 2.

With reference to FIGS. 1 and 2, the primary slit perforations 26 and 28 and secondary slit perforations 30, 34 and 38 define eight flap portions which, as later described, provide the access through the blanket 10. The two flap portions 64 are defined by the slit perforations 26, and the secondary slit perforations 30 and 34, and the heat seals 48 and the adhesive tapes 60, at the lower region of the blanket 10. The portions 66 define a second set of flap portions which are used when it is desired to have a maximum dimension access opening at the blanket lower region, and the flap portions 66 are defined by the heat seals 48, and slit perforations 30 and 34, and the flap portions 66 will pivot about a hinge line extending between the ends 32 and 36 of the slit portions 30 and 34, respectively.

In a similar manner, the flap portions 68 located adjacent the neck opening 22 are defined by the slit perforations 28, the secondary slit perforations 34 and 38, and the heat seals 50 and adhesive tapes 62. The flap portions 70 are defined by the heat seals 50, and the slit perforations 34 and 38, and will hinge about the hinge line defined between the slip perforation ends 36 and 40 of the slit perforations 34 and 38, respectively.

From the aforedescription, it is to be appreciated that when the maximum access opening is desired, the adjacent flap portions 64 and 66 will constitute a single major flap portion, and likewise, the adjacent flap portions 68 and 70 will define a single major flap portion, as later described.

Various blanket configurations capable of being defined from the previously described blanket structure will now be explained with respect to FIGS. 3–12 of the drawings.

Figure 3:
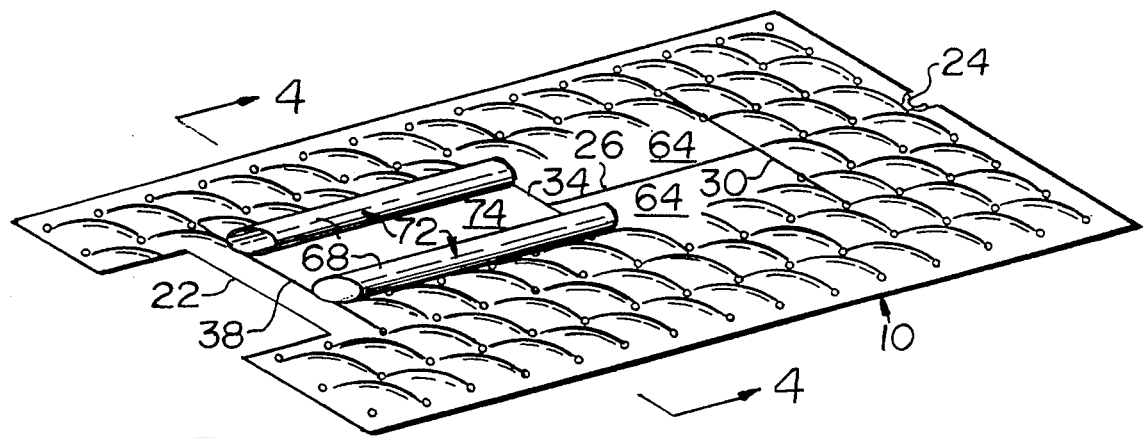
FIG. 3 is a perspective view of an inflated blanket illustrating a small access opening being defined in the blanket at the patient's chest region.

FIG. 3 illustrates the configuration of the blanket 10 when an access opening of limited length and width dimension is desired in the chest region of the patient. In such instance, the slit perforations 28 are opened along its length and slit perforations 34 and 38 are opened from slit 28 to heat seals 50 by manually fracturing the perforations defining these slits, and once the slit perforations 28, 34 and 38 are opened to form slits, it is possible to roll back the flap portions 68 to form the rolls 72 as will be apparent from FIGS. 3 and 4. In doing so, the adhesive tapes 58 will have their shields removed therefrom, so that the adhesive tapes or patches 58, once the rolls 72 are formed, can be made to adhere to the upper sheet 12 to maintain the configuration of the rolls 72 and provide access to the wearer's chest through access opening 74. Because of the heat seals 50, the flap portions 68 will not be inflated, and relatively tight concise rolls 72 may be formed between the secondary slits 34 and 38.

When forming the small rolls 72 to define a minimum chest space 74, the adhesive tapes 62 may have their shields removed therefrom wherein the adhesive faces of the tapes 62 can be used to adhere the lower portion of the roll 72 to the patient's body. Also, if desired, when placing the blanket 10 upon the patient, the adhesive tape shields located upon adhesive tapes 52 and 54 may be removed such that the adhesive faces thereof may adhere to the patient's body to position the blanket upon the body during the operation.

During the surgical operation, temperature controlled air will be supplied to the blanket 10 through the inlet fitting 24, and temperature controlled air will impinge upon the patient through the orifices 20 at all locations except at the space 74. At the termination of the operation, the blanket 10 may be removed from the patient and discarded, and a full blanket such as shown in U.S. Pat No. 5,125,238 may be placed upon the patient if continued thermal control is desired.

Figure 5:
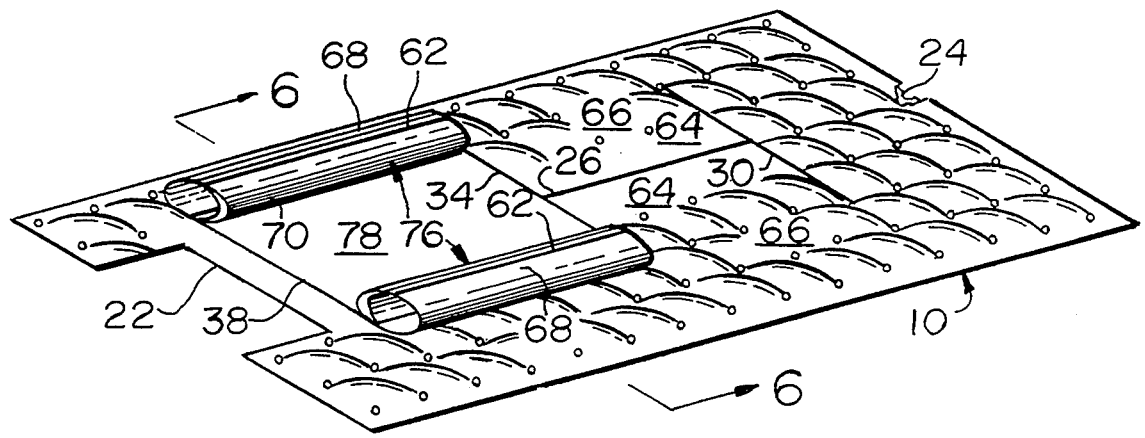
FIG. 5 is a perspective view of an inflated blanket illustrating the maximum size access opening being formed at the patient's chest region.
Figure 6:
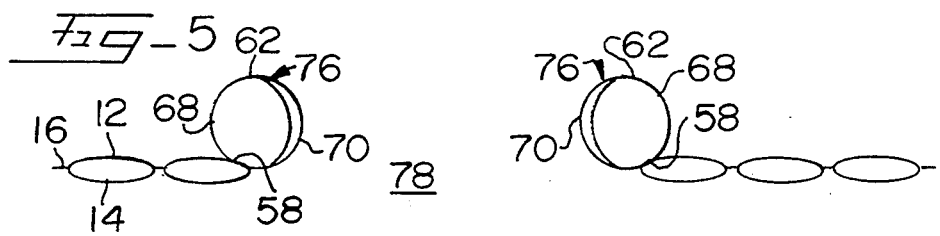
FIG. 6 is an elevational sectional view as taken through Section 6—6 of FIG. 5.

If it is desired that maximum access be available to the patient's chest region, the blanket configuration shown in FIGS. 5 and 6 is employed.

In FIGS. 5 and 6, the slit perforations 28 will be fully opened, as will the slit perforations 34 and 38 along their full lengths. This will permit the two major flap portions 68–70 to be folded back about the hinge lines between ends 36 and 40 to form rolls 76 of a larger dimension than rolls 72 produced with the arrangement of FIG. 3. The flap portions 70 will still be inflated, but the flap portions 68 are uninflated due to the heat seals 50, and the large dimension of the rolls 76 will produce a large space 78 for providing access to the wearer's chest region. By removing the adhesive face shields from the tapes 58, the tapes 58 can adhere to the upper sheet 12 as shown in FIG. 6, and the large configuration of the rolls 76 maintained. The shields on tapes 62 will not be removed.

Figure 4:
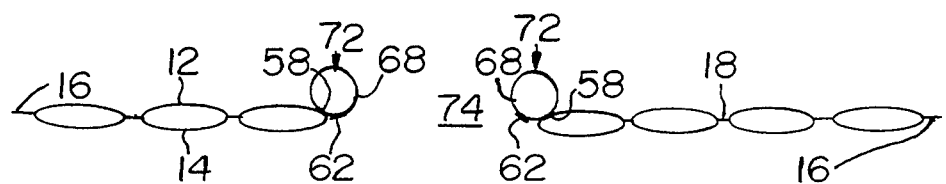
FIG. 4 is an elevational sectional view of the blanket as taken through Section 4—4 of FIG. 3.

In FIG. 7, an arrangement similar to that shown in FIGS. 3 and 4 is illustrated except that the access 80 provided to the wearer's chest region is not defined by rolls, in that the flap portions 68 are only pulled or folded back, rather than formed into rolls 72 such as shown in FIG. 3. The slit perforation 28, and half of the slit perforations 34 and 38 will be opened, and the flap portions 68 are only partially folded back away from each other. The adhesive tapes 62 may be used to adhere the blanket to the patient, but the adhesive face shields need not be removed from the adhesive tapes 58 as conventional surgical drapes may lay on the flap portions 68 to hold the flap portions down and out of the way during the operation. The arrangement of FIGS. 7 and 8 provides the access opening 80, but does not require that the flap portions 68 be formed into the rolls 72 as shown in FIGS. 3 and 4.

If it is desired to have a smaller opening access to the patient's abdomen, the blanket configuration shown in FIG. 9 is used. In this configuration, the slit perforation 26 is opened, and half of the perforations 30 and 34 are opened wherein the flap portions 64 may be formed into rolls 82, and by removing the adhesive shields from the tapes 56 the free ends of the flap portions 66 may be made to adhere to the blanket upper sheet 12 in the manner disclosed with respect to FIGS. 3 and 4. The access opening produced in this embodiment is indicated at 84.

If it is desired to have a larger opening at the patient's abdomen region, the slit perforations 30 and 34 will be fully opened along their length and the flap portion rolls will be made in a manner similar to that of the embodiment of FIGS. 5 and 6 to achieve a larger dimension access opening at the torso lower region.

In FIG. 10, a configuration of the blanket is illustrated wherein maximum diameter rolls 76 and 86 are produced to form a maximum access opening 88 extending between the patient's chest and abdomen. In this embodiment, the rolls 76 are formed in the manner described with respect to FIGS. 5 and 6, and the rolls 86 are formed in a like manner from the flap portions 64 and 66.

FIG. 11 illustrates another embodiment wherein a diamond shaped central opening is formed through the blanket 10. In this embodiment, the slit perforations 26 and 28 will be fully opened, as will the slit perforation 34. However, the flap portions 64–66 and 68–70 only adjacent the slit perforation 34 are fully rolled back, and by removing the adhesive face shields from the adhesive tapes 56 and 58, it is possible to define four conical shaped rolls 90, 92, 94 and 96 which will produce the diamond shaped access opening 98 in the central region of the blanket.

FIG. 12 discloses a blanket modification related to, but different, than the blanket 10 described in the previous embodiments. The blanket 99 is, basically, similar to the blanket 10, except that the blanket head end is indicated at 100 and the inlet port 102 for supplying the temperature controlled air to the blanket is located at the blanket head end. 104 represents the foot end of the blanket.

Secondary slit perforations are located in the blanket 99 at 106, 108 and 110, and the primary longitudinally extending slit perforation edge is represented at 111 in FIG. 12 in its rolled position. In this embodiment, adhesive tapes will be associated therewith in a manner similar to the embodiment previously described, and upon forming large rolls of the flap portions, rolls 112, 114 and 116 may be produced. As the slit perforation 111 extends to the foot end 104 of the blanket 99, a large access opening 118 having an open end 120 will result, and a blanket of this type is used in those instances wherein access to the lowermost regions of the patient's body is desired, while the patient is being subjected to temperature controlled air.

It is to be understood that in most uses of the blanket, the adhesive shields will be removed from the adhesive tapes 52 and 54 to adhere the blanket to the patient's body, and as to which adhesive faces are exposed, and which flap portions are to be displaced, is at the option of the operating room personnel. A disposable thermal blanket in accord with the inventive concepts is very versatile in its use, and yet the cost of manufacture and availability is low.

It is appreciated that various modifications to the inventive concepts may be apparent to those skilled in the art without departing from the spirit and scope of the invention.

We claim:

1. In a pneumatic, disposable, temperature control blanket having a periphery defined by a head end, a foot end, and lateral sides and having a central region, the blanket being formed by an envelope defined by an upper thermoplastic flexible air impervious sheet and a lower thermoplastic flexible sheet heat sealed together at the blanket periphery, a pneumatic flow chamber defined between the upper and lower sheets, an air inlet port defined in the envelope in communication with the flow chamber for supplying pressurized air thereto, and a plurality of spaced orifices defined in the lower sheet in communication with the flow chamber to convey temperature controlled air to the patient, the improvement comprising, a plurality of elongated access slits defined in the envelope in the blanket central region having opposite edges and extending through the upper and lower sheets forming envelope flap portions whereby said flap portions may be folded away from each other to provide open access through the envelope wherein said elongated access slits do not intersect the blanket periphery, and heat seals sealing said slits' opposite edges to prevent air loss at said slits.

2. In a pneumatic, disposable, temperature control blanket as in claim 1, wherein said slits include weak perforations initially holding said slits closed and the slits' opposite edges in contiguous relationship, said slits being opened and said slits' opposite edges being separated manually by fracturing said perforations.

3. In a pneumatic, disposable, temperature control blanket as in claim 2, said slits including a primary portion substantially parallel to said blanket periphery lateral sides and first and second spaced secondary portions transversely related to and intersecting said primary portion, said flap portions being located intermediate said slits' secondary portions.

4. In a pneumatic, disposable, temperature control blanket as in claim 3, said slits including third secondary portions spaced from said first and second secondary portions and transversely related to and intersecting said primary portion defining flap portions with adjacent secondary slit portions.

5. In a pneumatic, disposable, temperature control blanket as in claim 1, a plurality of exposable adhesive patches defined on the lower flexible sheet each having an adhesive face, and a removable shield mounted on each patch adhesive face whereby removal of the shield exposes the associated patch adhesive face.

6. In a pneumatic, disposable, temperature control blanket as in claim 5, said exposable adhesive patches being located on the lower sheet adjacent portions of said slits.

7. In a pneumatic, disposable, temperature control blanket as in claim 6, said adhesive patches being of an elongated linear configuration having a length substantially equal to the adjacent slit portion.

8. In a pneumatic, disposable, temperature control blanket having a periphery defined by a head end, a foot end, and lateral sides and having a central region, the blanket being formed by an envelope defined by an upper thermoplastic flexible air impervious sheet and a lower thermoplastic flexible sheet heat sealed together at the blanket periphery, a pneumatic flow chamber defined between the upper and lower sheets, an air inlet port defined in the envelope in communication with the flow chamber for supplying pressurized air thereto, a plurality of spaced orifices defined in the lower sheet in communication with the flow chamber to convey temperature controlled air to the patient, the improvement comprising, an elongated central primary slit defined in the blanket envelope central region having opposite edges and extending through the upper and lower sheets, said central slit being located between the blanket lateral sides and substantially parallel thereto and not intersecting the blanket periphery, first and second secondary elongated slits defined in the envelope each having opposite edges and extending through the upper and lower sheets, said secondary slits transversely intersecting said central slit at spaced locations along its length and forming a flap portion in the envelope between said secondary slit portions which may be folded back to provide access through the envelope, and flexible seals sealing said slits' opposite edges to prevent air loss at said slits.

9. In a pneumatic, disposable, temperature control blanket as in claim 8, said flexible seals sealing said slits' opposite edges comprising continuous heat seals sealing said upper and lower sheets together adjacent said slits' opposite edges.

10. In a pneumatic, disposable, temperature control blanket as in claim 9, said secondary slits each extending through said central slit whereby said secondary slits define flap portions on each side of said central slit which may be folded away from each other.

11. In a pneumatic, disposable, temperature control blanket as in claim 10, a third secondary slit defined in the blanket envelope having opposite edges and extending through the upper and lower sheets transversely intersecting and extending through said central slit, said third secondary slit being spaced from said second secondary slits with respect to the length of said central slit whereby flap portions are defined in the envelope between said second and third secondary slits on opposite sides of said central slit.

12. In a pneumatic, disposable, temperature control blanket as in claim 11, said first and third secondary slits intersecting and defining ends of said central slit, an exposable adhesive patch having an adhesive face defined upon the lower sheet adjacent to said first and third secondary slits and on the opposite side thereof with respect to said central slit, and a removable shield mounted on each adhesive patch adhesive face whereby removal of the shield exposes the associated adhesive face.

13. In a pneumatic, disposable, temperature control blanket as in claim 12, said adhesive patches being of an elongated linear configuration and of a length substantially equal to the length of the adjacent secondary slit.

14. In a pneumatic, disposable, temperature control blanket as in claim 15, an elongated adhesive patch having an adhesive face defined upon the lower sheet adjacent said central slit upon each opposite edge thereof, and a removable shield mounted on each adhesive patch adhesive face upon said central slit opposite edges whereby removal of the shield exposes the associated adhesive face and said flap portions can adhere to the upper sheet when folded away from the central slit.

15. In a pneumatic, disposable, temperature control blanket as in claim 14, said elongated adhesive patches defined upon the lower sheet upon said central slit opposite edges being linear and parallel to each other and of a length substantially equal to the spacing between adjacent secondary slits.

16. In a pneumatic, disposable, temperature control blanket as in claim 15, an outer elongated linear adhesive patch having an adhesive face defined upon the lower sheet substantially parallel to each adhesive patch located at said central slit opposite edges and spaced therefrom extending between adjacent secondary slits, a removable shield mounted on each outer adhesive patch adhesive face whereby removal thereof exposes the associated adhesive face, said outer adhesive patch permitting said lower sheet to adhere to the patient's body upon said flap portions being folded away from said central slit, and an elongated heat seal sealing the upper and lower sheets together adjacent said outer adhesive patches whereby the portions of said flap portions between said central slit and said outer adhesive patches will be uninflated to facilitate folding of said flap portions.

17. In a pneumatic, disposable, temperature control blanket as in claim 8, wherein said slits include weak perforations initially holding said slits closed and the slits' opposite edges in contiguous relationship, said slits being opened and said slits' opposite edges being separated manually by fracturing said perforations.

18. In a pneumatic, disposable, temperature control blanket as in claim 8, a plurality of exposable adhesive patches defined on the lower sheet each having an adhesive face, and a removable shield mounted on each patch face whereby removal of the shield exposes the associated adhesive face.

19. In a pneumatic, disposable, temperature control blanket as in claim 18, said exposable adhesive patches being located on the lower sheet adjacent portions of said slits.

20. In a pneumatic, disposable, temperature control blanket as in claim 19, said adhesive patches being of an elongated linear configuration having a length substantially equal to the adjacent slit portion.

* * * * *